United States Patent
Benchetrit

(10) Patent No.: US 7,488,336 B2
(45) Date of Patent: Feb. 10, 2009

(54) SINGLE CONTROL GASTRIC BAND

(75) Inventor: Salomon Benchetrit, Caluire (FR)

(73) Assignee: Compagnie Europeenne d'etude et de Recherche de Dispositifs pour l'Implatation par Laporoscopie, Vienne (FR)

( * ) Notice: Subject to any disclaimer, the term of this patent is extended or adjusted under 35 U.S.C. 154(b) by 324 days.

(21) Appl. No.: 10/181,469

(22) PCT Filed: Jan. 19, 2001

(86) PCT No.: PCT/FR01/00185

§ 371 (c)(1), (2), (4) Date: Nov. 6, 2002

(87) PCT Pub. No.: WO01/52777

PCT Pub. Date: Jul. 26, 2001

(65) Prior Publication Data

US 2003/0158564 A1    Aug. 21, 2003

(30) Foreign Application Priority Data

Jan. 20, 2000 (FR) .................................. 00 00693

(51) Int. Cl.
*A61B 17/08* (2006.01)
(52) U.S. Cl. ........................... 606/157; 606/151
(58) Field of Classification Search ............. 606/151, 606/157, 158, 153; 24/17 AP, 16 PB, 30.5 R, 24/30.5 P See application file for complete search history.

(56) References Cited

U.S. PATENT DOCUMENTS

| 4,592,339 | A | * | 6/1986 | Kuzmak et al. | 128/899 |
|---|---|---|---|---|---|
| 5,074,868 | A | | 12/1991 | Kuzmak | 606/157 |
| 5,152,770 | A | * | 10/1992 | Bengmark et al. | 606/157 |
| 5,160,338 | A | * | 11/1992 | Vincent | 606/157 |
| 5,226,429 | A | * | 7/1993 | Kuzmak | 128/898 |
| 5,449,368 | A | * | 9/1995 | Kuzmak | 606/157 |
| 5,601,604 | A | * | 2/1997 | Vincent | 606/216 |
| 5,910,149 | A | * | 6/1999 | Kuzmak | 606/157 |
| 6,102,922 | A | * | 8/2000 | Jakobsson et al. | 606/157 |
| 6,916,326 | B2 | * | 7/2005 | Benchetrit | 606/151 |

FOREIGN PATENT DOCUMENTS

| DE | G9014048.6 U1 | 12/1990 | |
| DE | 19751733 | * 12/1998 | 606/157 |
| EP | 0611561 A1 | 8/1994 | |
| WO | WO 94/27504 | 12/1994 | |

* cited by examiner

*Primary Examiner*—Eduardo C Robert
*Assistant Examiner*—Mary Hoffman
(74) *Attorney, Agent, or Firm*—Thomas, Kayden, Horstemeyer & Risley, LLP

(57) ABSTRACT

The invention relates to a gastroplasty ring formed by a flexible strip (2) for passing around the stomach and for being closed near its two end portions (5, 6) by a closure system (7, 12, 13, 15, 20) to reduce the diameter of the opening of the stoma, said strip having an annular compression chamber of adjustable volume and of substantially constant section that is connected by an adjustment catheter (7) to a device (8) for adjusting the internal pressure in said chamber so as to adjust its diametral expansion, the ring being characterized in that the closure system includes means (12, 13) for locking and loosening the ring, which means are carried by the adjustment catheter, thus making it possible, starting from the position in which the diameter of the ring is locked, to release the diameter of the ring by relative displacement between the two end portions. The ring constitutes a gastric implant for treating obesity.

10 Claims, 1 Drawing Sheet

SINGLE CONTROL GASTRIC BAND

CROSS REFERENCE RELATED APPLICATIONS:

This application is a national phase of PCT/FR01/00185 filed Jan. 19, 2001, which claims priority to French Application Serial No. 00/00693 filed Jan. 20, 2000.

TECHNICAL FIELD

The present invention relates to the technical field of surgical implants for treating obesity by implanting a flexible gastric strip for constricting the stomach of a patient, said gastric strip being provided with an annular compression chamber of variable volume that is adjustable by means of an adjustment catheter connected to a control and adjustment device implanted in the body of the patient.

The present invention relates to a gastroplasty ring formed by a flexible strip for passing around the stomach and for being closed near its two end portions, using a closure system to reduce the diameter of the opening of the stoma, said strip having an annular compression chamber of adjustable volume that is connected by an adjustment catheter to a device for adjusting the internal pressure in said chamber so as to adjust its diametral expansion.

PRIOR ART

For patients suffering from extremely severe obesity (morbid obesity), i.e. for patients whose weight exceeds the ideal weight by at least 50 kilograms, for example, it is absolutely essential to operate surgically on such patients in order to avoid not only a series of health problems that stem from such obesity, but also to avoid certain and imminent death of such patients.

It is accepted that patients suffering morbid obesity have life expectancy that is significantly reduced, by at least ten to fifteen years, while also giving rise to severe psychological problems. Furthermore, a whole series of associated health phenomena are involved, having an effect on the appearance of cardiovascular disease, hypertension, diabetes, and severe arthritis, in particular.

It has also been observed that treatment based on a severe diet combined with a series of physical exercises associated with a change in behavior, in particular eating behavior, are relatively ineffective in such cases of morbid obesity, even though such methods of treatment are the most healthy.

That is why effective long-term treatment of morbid obesity can involve surgical treatment.

In general, surgical treatment techniques can be divided into those which cause food to be absorbed poorly, i.e. shortening the conventional path followed by food and digestive juices, and techniques that make use of gastric restriction, i.e. reducing the size of the stomach.

By way of example, surgical techniques that rely on poor absorption are those that imply a technique of bypassing the small intestine or those, which separate the paths followed by food and digestive juices. The bypass surgical technique gives rise to severe complications, such that that technique is now used only very rarely. The surgical technique whereby the path followed by the alimentary bolus is separated from that of the digestive juices does not give rise to particular complications, but it does require major surgery, and in particular it implies partial gastrectomy.

That is why present trends are towards using surgical techniques that implement gastric restriction to reduce food intake.

In conventional manner, such techniques make use of gastropiasty rings implanted around the stomach to reduce its size and the diameter of its passage (stoma).

Most known gastroplasty devices, for example the device described in patent U.S. Pat. No. 5,074,868, make use of a flexible strip made of elastomer material that is implanted around the stomach and then tightened and closed to form a loop of fixed diameter by means of a closure system. The body of the flexible strip includes a variable volume compression cavity or chamber that is connected by an adjustment catheter to a device for adjusting the internal pressure of the chamber so as to vary the internal diameter of the loop and thus modify or adjust the diameter of the stoma by injecting or extracting a volume of liquid into or from the chamber. Such an operation of adjusting the inside diameter of the ring is performed by means of conventional control devices including a miniature unit implanted directly beneath the skin of the patient and provided with a self-closing membrane through which the doctor injects or withdraws liquid by means of a syringe.

The closure system of patent U.S. Pat. No. 5,075,868 makes use of suture thread for suturing together the two strands of the flexible strip constituting the ring.

Such a device generally gives satisfaction, but like most known systems it suffers from drawbacks associated essentially with the difficulty of any surgical operation that may need to be performed after the gastroplasty implant has been into place. In spite of the possibility of modifying the diameter of the ring to some extent without a surgical operation by means of the above-mentioned miniature unit, it turns out that implanting such gastric implants can be accompanied by phenomena of intolerance, e.g. can be accompanied by vomiting, associating with the diameter of the stoma being reduced excessively, or they can be associated with the implant being ineffective in its action because the diameter of the stoma is too large, or indeed they can be associated merely with local or general inflammation or infection or discomfort.

That is why it is often necessary to operate surgically again either to relieve the patient or to modify or change a previously implanted gastroplasty ring. Such surgical operations are particularly difficult and further require the surgeon to cut either the ring, or as in the case of patent U.S. Pat. No. 5,074,868, the suture thread so as to open the ring completely and then change it or replace it.

Such operations are awkward to perform, poorly tolerated by the patient, and expensive, particularly in that they imply the destruction of an implant and its replacement. In addition, in the case of patent U.S. Pat. No. 5,074,868, the device for assisting in cutting the suture makes the surgical implant relatively complex to manufacture and make up, without genuinely providing much real help during the operation.

Utility model DE-G-90 14048 describes a partially annular system specifically designed and adapted to totally closing blood vessels, and its teaching is not directly transposable to compressing the stomach which must be done under full control.

SUMMARY OF THE INVENTION

Consequently, the object given to the invention is to propose a novel gastroplasty ring making it possible to remedy the various drawbacks mentioned above and capable of facilitating surgical operations any subsequent surgical operations after the implant has been implanted, without requiring the implant to be replaced, and with the implant in any event being of particularly simple design that is easy to make.

Another object of the invention is to propose a novel gastroplasty ring capable in simple and reliable manner of reversibly closing the loop that constitutes the ring.

Another object of the invention is to propose a novel gastroplasty ring suitable for providing simple and reliable means for adapting and finely adjusting the diameter of the ring to each particular surgical situation.

Another object of the invention is to propose a novel gastroplasty ring suitable for presenting a plurality of implantation diameters.

Another object of the invention is to propose a novel gastroplasty ring making it easier to thread the catheter.

Another object of the invention is to propose a novel gastroplasty ring that is particularly easy to manufacture while also providing excellent general strength.

The objects given to the invention are achieved by means of a gastroplasty ring formed by a flexible strip for passing around the stomach and for being closed near its two end portions by a closure system to reduce the diameter of the opening of the stoma, said strip having an annular compression chamber of adjustable volume and of substantially constant section that is connected by an adjustment catheter to a device for adjusting the internal pressure in said chamber so as to adjust its diametral expansion, the ring being characterized in that the closure system includes means for locking and loosening the ring, which means are carried by the adjustment catheter, thus making it possible, starting from the position in which the diameter of the ring is locked, to release the diameter of the ring by relative displacement between the two end portions.

BRIEF SUMMARY OF THE DRAWINGS

Other objects and advantages of the invention will appear better on reading the following description of one of its embodiments, and from the accompanying drawings given purely for illustration and information, in which.

BEST MANNER OF PERFORMING THE INVENTION

Figure 1:
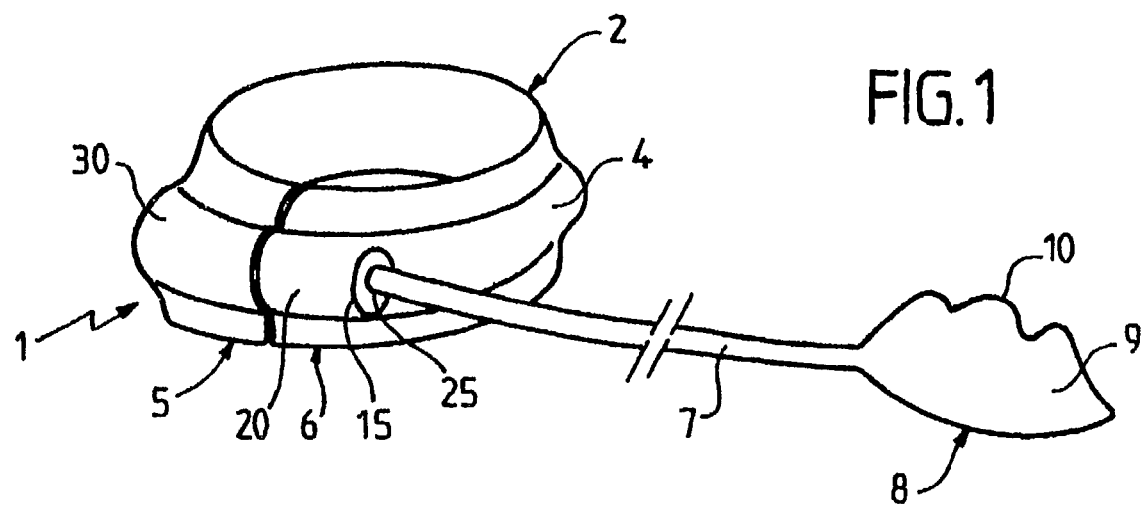
FIG. 1 is a diagrammatic perspective view of an embodiment of a gastroplasty ring of the invention shown in the closed position.
Figure 2:
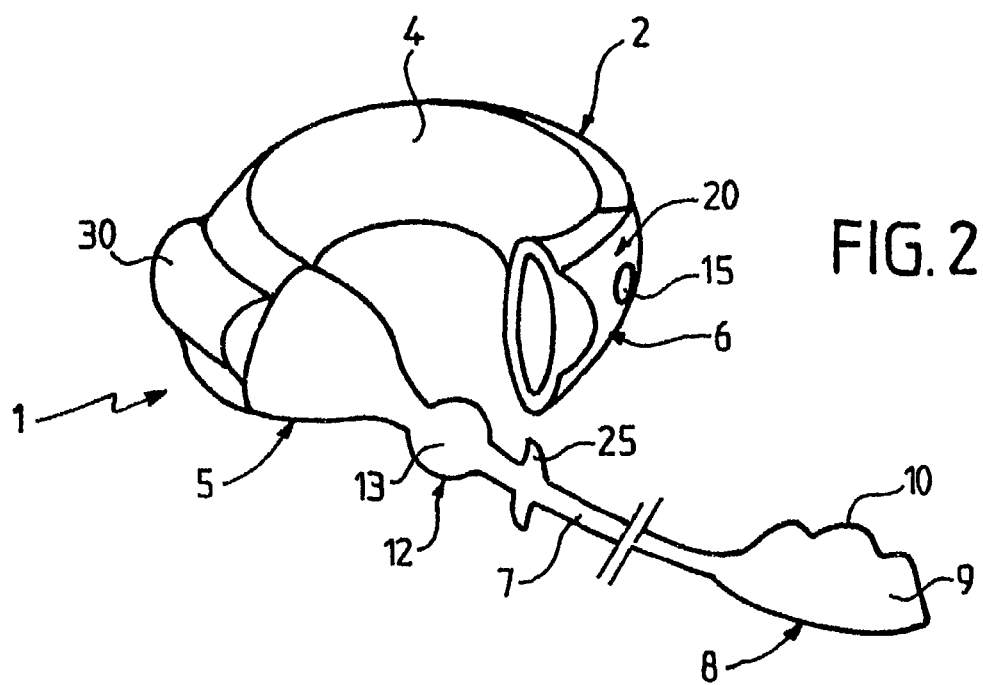
FIG. 2 is a diagrammatic perspective view of an embodiment of a gastroplasty ring of the invention in the open position prior to being implanted.
Figure 3:
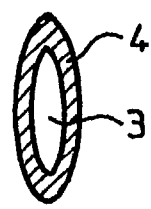
FIG. 3 is a cross-section view showing the section of the gastroplasty ring of the invention.

FIGS. 1 and 2 show a preferred embodiment of a gastroplasty ring 1 of the invention formed by a flexible strip 2 made, for example, by thermoforming an elastomer material for surgical use. The strip 2 defines an internal compression chamber 3 that preferably extends substantially over its entire length, the chamber being defined by the walls 4 of the flexible strip 2 and by two end portions 5 and 6. In its position when implanted around the stomach of a patient, as shown in FIG. 1, the compression chamber 3 thus forms an annular compression chamber of section and profile that are adapted to avoid forming any pinch zones that could nip the walls of the stomach. This implies in particular that it has a contact surface with the stomach that is continuous and uniform and that an annular compression zone is formed that is almost perfect, excluding in particular any droplet shape that might damage cellular tissue.

As is well known in the prior art, the compression chamber 3 defines a closed volume inside the gastroplasty ring, for the purpose of forming a volume that is adjustable so as to adjust the diametral expansion of the ring while it is in place in order to adapt it to each particular surgical situation.

In conventional manner, the diametral expansion of the gastroplasty ring of the invention is adjusted by an adjustment catheter 7 formed by a tubular element of elastomer material extending one of the free end portions, e.g. the end portion 5, of the compression chamber 3 so as to connect said chamber to a device 8 for adjusting the internal pressure of said chamber.

As is well known to the person skilled in the art, the adjustment device 8 can be formed by a miniature unit 9 that is implanted beneath the skin of the patient. By way of example, the miniature unit 9 has a self-sealing membrane 10 on top for being pierced by a syringe so as to inject or withdraw a certain quantity of fluid (e.g. distilled water) for the purpose of varying the volume of the compression chamber 3, to adjust the volume of the chamber and thus obtain the desired internal diameter for the ring. Since such a device is well known to the person skilled in the art, it is not described in greater detail herein.

The gastroplasty ring of the invention also has a closure system enabling it to be closed and serving to hold the gastroplasty ring looped in position around the stomach.

According to an important characteristic of the invention, the closure system of the invention includes means for locking and loosening the ring, which means are carried by the adjustment catheter 7, i.e. form an integral part of said catheter and make it possible starting from the closed position shown in FIG. 1 where the ring is looped with a locked diameter, to release its diameter momentarily by allowing the two end portions 5, 6 of the ring to move relative to each other, while nevertheless forming, if desired, a closed loop around the stomach. The locking and loosening means are advantageously reversible.

In the invention, the locking and loosening means include pneumatic means to ensure the closure and opening of the ring, e.g. by making use of fluid, gas, or liquid. The use of pneumatic means enables the implant to be installed more simply and to be opened and closed using a single control.

In addition to simplifying the installation and closure of the ring, providing this technical function makes it possible to reduce the severity and the extent of any subsequent surgical operations after an implant has been put into place by avoiding the need to section and destroy the installed gastroplasty ring. Such a function makes it possible to leave the ring in place while merely momentarily increasing its diameter without destroying the loop of the ring, thus making it possible subsequently to retighten the ring so as to return it to the closed position as shown in FIG. 1.

In a preferred variant of the invention, as shown in FIGS. 1 and 2, the gastroplasty ring of the invention includes a closure system having reversible locking and loosening means that include at least one deformable zone 12 formed or provided on the adjustment catheter 7, and an opening 15 made in the wall 4 of the end portion 6 of the strip 2. The inflatable adjustable catheter 7 which is made of biocompatible elastomer material is intended to be threaded through the opening 15 in the closed ring position and is also intended to serve as guide means.

The deformable zone 12 is suitable for forming a projection 13 when the pressure inside the adjustable catheter 7 is increased, said projection 13 bearing against the walls 4 of the end portion 6 of the strip, inside the chamber 3, to lock the ring in the closed position. The projection 13 returns to its rest shape if the pressure inside the adjustment catheter 7 returns to normal, thereby allowing the said catheter to slide and be guided freely through the opening 15, thus loosening the loop.

In a particularly advantageous version of the invention, the reversible deformation zone 12 is formed by at least one zone 13 of weakness and in its rest shape it constitutes a projection relative to the remainder of the section of the adjustment catheter 7. In other words, the cross section of the deformable zone 12 at rest has an area that is greater than that of the cross section of the remaining length of the adjustment catheter 7 so as to form a slight swelling on the surface of the catheter.

Advantageously, the deformable zone 12 can be constituted by a section of the adjustment catheter 7 having elastomer material constituting the catheter presenting hardness which is locally less than the general hardness of said catheter. Under such circumstances, the adjustment catheter 7 is connected to the external adjustment device 8 for being pressurized by means of a fluid (air or liquid), and the zone 12 tends to form a balloon 13 of diameter greater than the inside dimensions of the strip, thereby locking the diameter of the ring. The balloon is pressurized before the strip.

Naturally, and in a variant, a gastroplasty ring of the invention could have a plurality of weak zones 12 spaced apart in optionally regular manner along the adjustment catheter 7 to make up a gastroplasty ring capable of occupying a plurality of fixed diameters when in position.

Advantageously, the flexible strip 2 is provided at one end portion, e.g. at its end portion 6 opposite its end portion 5 which is extended by the adjustment catheter 7, with a hollow sleeve 20 extending the flexible strip 2.

The hollow sleeve 20 also has the opening 15 which is provided in one of its face (preferably an outside face) so as to enable the other end 5 of the flexible strip 2 to be inserted into said sleeve in the closed position with the adjustment catheter 7 then passing through the opening 15 so as to loop the ring. This structural disposition ensures that closure is reliable and long lasting, while also enabling the compression chamber 2 to extend over the entire perimeter over which the stomach is constrained.

The strip 2 and the hollow sleeve 20 are preferably oblong in cross-section to make the deformable zone 12 even easier to jam when it is pressurized.

Advantageously, the flexible strip 2, the compression chamber 3, and the hollow sleeve 20 form a single piece made out of the same elastomer plastic material, the adjustment catheter 7 being subsequently heat-sealed thereto.

In advantageous manner, it is also possible to make the deformable zone 12 with a thickness that is different from the thickness of the flexible strip 2 so as to obtain different fluid flow rates in each of these elements. The different flow rates can also be obtained by different shapes, thereby enabling the flexible strip 2 to be deflated before the deformable zone 12, for example.

The end portion 5 of the strip 2 to which the adjustment catheter 7 is connected is preferably cone shaped to facilitate inserting said catheter into the hollow sleeve 20. The deformable zone 12 is situated in the vicinity of the narrower portion of said cone shape.

The adjustment catheter 7 preferably has visual location means 25 which are situated at a distance from the deformable zone 12 and which are intended, when the projection 13 is in the locked position, to pass through the opening 15 of the hollow sleeve 20. The visual location means 25 consist, for example, of a ring having a diameter that is greater than that of the catheter. They make it possible to verify that the catheter has been threaded far enough through the opening 15 and they also make it possible to ensure that the projection 13 is held in position when locked in the hollow sleeve 20.

Furthermore, the adjustment catheter 7 is substantially rigid and is long relative to the diameter of the ring to make it easier to thread the catheter 7 and pass it through the opening 15. This also enables good positioning of the strip in the desired position. To facilitate threading, it is possible to make the adjustment catheter 7 with an end portion that is harder than its portion adjacent to the projection 13, the harder portion then being sectioned after threading.

To further facilitate good positioning of the strip, said strip has handling means 30 on its wall 4, which handling means consist of a surplus of material placed on the surface of said wall.

In a variant embodiment not shown in the figures, the closure system also includes female means placed inside the hollow sleeve 20 with a view to further improving locking of the projection 13. In this variant, the female means is in the form of an eyelet against which the projection 13, or the balloon, expands and is locked in position under the effect of the pressure.

Making a gastroplasty ring as a single piece simplifies the method of manufacturing the ring and makes it possible to obtain a ring that avoids any risk of coming apart over time.

While the ring of the invention is being put into place around the stomach, it is in the position as shown in FIG. 2. The adjustment device 8 is initially disconnected and the surgeon threads and passes the adjustment catheter 7 through the opening 15 so as to insert the end 5 in the hollow sleeve 20 (FIG. 1). If necessary, the surgeon then reduces the length of the adjustment catheter 7 by sectioning the harder portion as identified by a visual marker. Thereafter, the surgeon can use the adjustment and inflation device 8 connected to the single catheter 7 to lock the ring in position after making sure that the weak zone 12 corresponding to the diameter desired for the implant is properly positioned inside the sleeve 20, visual inspection being performed by means of the ring 25. Thereafter, the surgeon can adjust the inside diameter of the ring by injecting or withdrawing the appropriate quantity of liquid through the catheter 7. It should be observed that all of the operations are performed using a single catheter 7.

In the event of a subsequent surgical operation, the gastroplasty ring of the invention makes it possible to limit the operation to examining the outside surface of the implant in position by celioscopy or laparoscopy, merely using a camera for optical inspection. If circumstances require it, it is possible initially, merely by celioscopy, to reduce the pressure in the catheter 7, thereby releasing the balloon 13 and allowing the catheter to slide through the opening 15 given that this catheter is of sufficient length. Such sliding is accompanied by momentary and partial loosening of the ring without it being necessary to perform major surgery on the patient. Thereafter, still merely by laparoscopic examination and intervention, it is possible to reclose and relock the ring in the closed position in very simple manner since the loop of the ring has never been undone.

SUSCEPTIBILITY OF INDUSTRIAL APPLICATION

The industrial application of the invention lies in designing and using gastroplasty rings.

The invention claimed is:

1. A gastroplasty ring comprising a flexible strip having two end portions for passing around a stomach and for being closed near said two end portions, a closure system for reducing the diameter of the opening of a stoma, said strip having an annular compression chamber of adjustable volume, a device for adjusting the internal pressure in said chamber so as to adjust its diametral expansion, with an adjustment catheter connected to said chamber and to said device, said closure system having means for locking and loosening said ring including a hollow walled sleeve provided in said strip at a first end portion, at least one deformable zone formed on said adjustment catheter, and an opening formed in the wall of said sleeve, said adjustment catheter being capable of sliding in said sleeve and through said opening to loop said ring, said deformable zone capable of expanding under increased pressure introduced by said device and bearing against said sleeve to lock said ring in a closed position, and capable of returning to an unexpanded state under a reduction in pressure to allow said catheter to slide freely and loosen the loop to release the diameter of the ring by relative displacement between said two end portions while maintaining the loop.

2. The ring according to claim 1, in which the deformable zone is a weak zone formed in the adjustment catheter, and which, at rest, projects outwardly relative to the remainder of the adjustment catheter.

3. The ring according to claim 2, in which a second end portion of the strip can be inserted into the sleeve.

4. The ring according to claim 3, in which said second end portion of the flexible strip is of converging shape and includes a local projection is situated in the vicinity of said second end portion.

5. The ring according to claim 4, in which the adjustment catheter also includes a visual location means which is situated at a distance from the deformable zone and which is intended, when the closure means are in the closed position, to pass through the opening of the sleeve.

6. The ring according to claim 5, in which the locking and loosening means include a pneumatic means making use of a fluid means selected from the group consisting of a gas and a liquid.

7. The ring according to claim 6, in which a cross-section of the strip is oblong.

8. The ring according to claim 6, in which the adjustment catheter is substantially rigid and is long relative to the diameter of the ring to make it easier to pass the catheter through the opening.

9. The ring according to claim 1, in which the strip includes, on is an outside wall, a handling means intended to facilitate manipulation of the ring.

10. A gastroplasty ring comprising a flexible strip having two end portions for passing around a stomach and for being closed near said two end portions, a closure system for reducing the diameter of the opening of a stoma, said strip having an annular compression chamber of adjustable volume, a device for adjusting the internal pressure in said chamber so as to adjust its diametral expansion, with an adjustment catheter connected to said chamber and to said device for pressurizing and depressurizing the adjustment catheter, said closure system having means for locking and loosening said ring including a hollow walled sleeve provided in said strip at a first end portion, at least one deformable zone formed on said adjustment catheter, and an opening formed in the wall of said sleeve, said adjustment catheter being capable of sliding in said sleeve and through said opening to loop said ring, said deformable zone capable of expanding under increased pressure introduced by said device and bearing against said sleeve to lock said ring in a closed position, and capable of returning to an unexpanded state under a reduction in pressure to allow said catheter to slide freely and loosen the loop to release the diameter of the ring by relative displacement between said two end portions while maintaining the loop.

\* \* \* \* \*